US012697044B2

(12) United States Patent
Devery et al.

(10) Patent No.: US 12,697,044 B2
(45) Date of Patent: Aug. 4, 2026

(54) BIOSENSORS FOR THE GASTROINTESTINAL TRACT

(71) Applicant: ENTERASENSE LIMITED, Galway (IE)

(72) Inventors: Donal Devery, Galway (IE); Maria Chiara Di Carlo, Galway (IE)

(73) Assignee: ENTERASENSE LIMITED, Galway (IE)

( * ) Notice: Subject to any disclaimer, the term of this patent is extended or adjusted under 35 U.S.C. 154(b) by 362 days.

(21) Appl. No.: 18/560,945

(22) PCT Filed: May 18, 2022

(86) PCT No.: PCT/EP2022/063491
§ 371 (c)(1),
(2) Date: Nov. 15, 2023

(87) PCT Pub. No.: WO2022/243395
PCT Pub. Date: Nov. 24, 2022

(65) Prior Publication Data
US 2024/0252059 A1 Aug. 1, 2024

(30) Foreign Application Priority Data

May 20, 2021 (EP) ..................................... 21175002

(51) Int. Cl.
A61B 5/07 (2006.01)
A61B 5/00 (2006.01)
(Continued)

(52) U.S. Cl.
CPC ............ A61B 5/073 (2013.01); A61B 5/0013 (2013.01); A61B 5/0028 (2013.01);
(Continued)

(58) Field of Classification Search
CPC ..... A61B 5/073; A61B 5/0013; A61B 5/0028; A61B 5/0075; A61B 5/0084; A61B 5/01;
(Continued)

(56) References Cited

U.S. PATENT DOCUMENTS

2004/0171915 A1 9/2004 Glukhovsky et al.
2005/0004474 A1* 1/2005 Iddan ................... A61B 1/0607
600/476
(Continued)

FOREIGN PATENT DOCUMENTS

WO 2010086859 A1 8/2010
WO 2012030977 A1 3/2012
(Continued)

OTHER PUBLICATIONS

International Search Report issued in PCT/EP2022/063491; mailed Dec. 2, 2022.
(Continued)

*Primary Examiner* — Niketa Patel
*Assistant Examiner* — Sebastian X Lukjan
(74) *Attorney, Agent, or Firm* — Studebaker Brackett PLLC

(57) ABSTRACT

A biosensor capsule having a generally cylindrical housing with a plurality of sensors including a radiation sensor including a radiation emitter and a radiation detector and at least one additional sensor. A processor uses data feeds from the radiation sensor and also from one more additional sensor of a different type. Additional sensors may be pressure or pH sensors to provide sensor signals to detect location along the GI tract in use. There may be a camera, and data derived from other sensors may be embedded in a video feed timeline. The capsule may have an asymmetric weight distribution to help keep sensing parts immersed in liquid.

19 Claims, 9 Drawing Sheets

(51) Int. Cl.

| | |
|---|---|
| *A61B 5/01* | (2006.01) |
| *A61B 5/02* | (2006.01) |
| *A61B 5/06* | (2006.01) |
| *A61B 5/145* | (2006.01) |

(52) U.S. Cl.

CPC .......... *A61B 5/0075* (2013.01); *A61B 5/0084* (2013.01); *A61B 5/01* (2013.01); *A61B 5/02042* (2013.01); *A61B 5/065* (2013.01); *A61B 5/14503* (2013.01); *A61B 5/14507* (2013.01); *A61B 5/14539* (2013.01); *A61B 5/6852* (2013.01); *A61B 5/7221* (2013.01); *A61B 5/7271* (2013.01); *A61B 5/743* (2013.01); *A61B 5/4238* (2013.01); *A61B 5/4255* (2013.01); *A61B 2560/0462* (2013.01); *A61B 2562/0233* (2013.01); *A61B 2562/0247* (2013.01); *A61B 2562/0271* (2013.01); *A61B 2562/043* (2013.01); *A61B 2562/162* (2013.01)

(58) Field of Classification Search

CPC . A61B 5/02042; A61B 5/065; A61B 5/14503; A61B 5/14507; A61B 5/14539; A61B 5/6852; A61B 5/7221; A61B 5/7271; A61B 5/743; A61B 5/4238; A61B 5/4255; A61B 2560/0462; A61B 2562/0233; A61B 2562/0247; A61B 2562/0271; A61B 2562/043; A61B 2562/162; A61B 5/036

See application file for complete search history.

(56) References Cited

U.S. PATENT DOCUMENTS

| | | | | |
|---|---|---|---|---|
| 2005/0228308 | A1* | 10/2005 | Iddan | ................... A61B 5/0031 600/561 |
| 2007/0032699 | A1 | 2/2007 | Segawa et al. | |
| 2007/0060798 | A1 | 3/2007 | Krupnik et al. | |
| 2008/0064938 | A1* | 3/2008 | Semler | .................... A61B 5/06 600/309 |
| 2013/0304446 | A1 | 11/2013 | Rabinovitz et al. | |
| 2015/0150437 | A1 | 6/2015 | Date et al. | |
| 2019/0150841 | A1* | 5/2019 | Terry | ................. A61B 10/0283 |
| 2020/0330004 | A1 | 10/2020 | Wahid et al. | |
| 2021/0259583 | A1* | 8/2021 | Sorgenfrei | ........... A61B 5/4064 |

FOREIGN PATENT DOCUMENTS

| | | |
|---|---|---|
| WO | 2013088444 A2 | 6/2013 |
| WO | 2020212538 A1 | 10/2020 |
| WO | 2021007622 A1 | 1/2021 |

OTHER PUBLICATIONS

Cummins et al.: "Gastrointestinal diagnosis using non-white light imaging capsule endoscopy", Nature Reviews Gastroenterology & Hepatology, Nature Publishing Group UK, London, vol. 16, No. 7, Apr. 16, 2019, pp. 429-447.

* cited by examiner

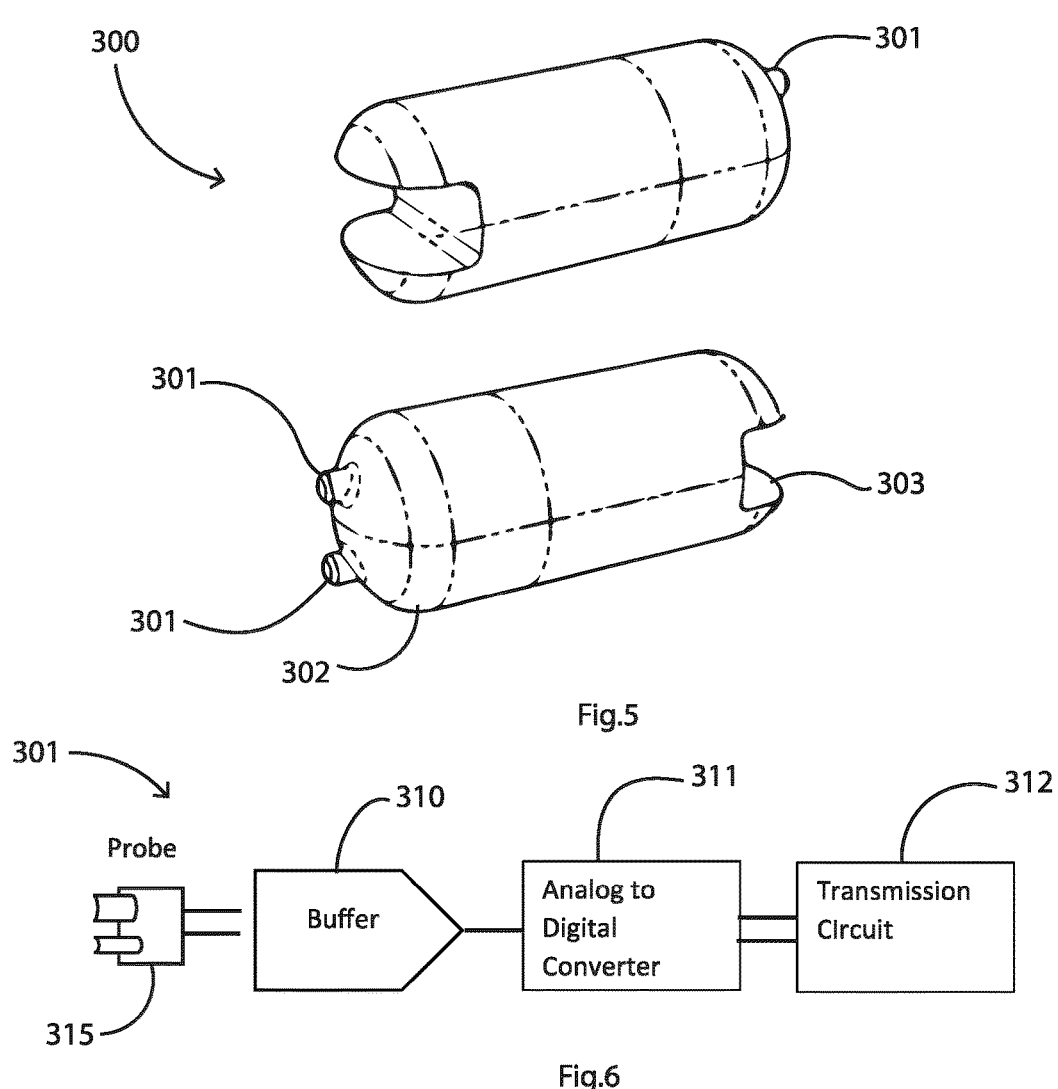
Fig.5
Fig.6
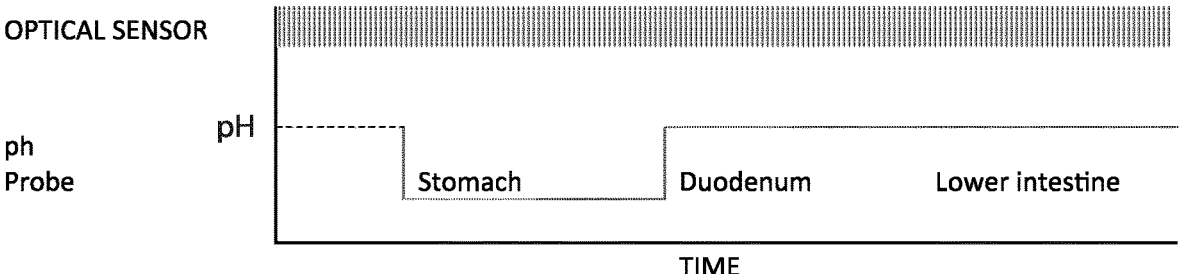
Fig.7

BIOSENSORS FOR THE GASTROINTESTINAL TRACT

BACKGROUND OF THE INVENTION

The present invention relates to biosensors for detecting conditions such as blood presence in the GI tract.

Our prior patent specification WO2020/212538, the contents of which are incorporated by reference, describes biosensor capsules.

The present invention is directed towards providing for enhanced data capture from such sensors.

SUMMARY OF THE INVENTION

Described here are devices, methods, and systems useful for detecting conditions in the gastrointestinal tract.

We describe a biosensor comprising:
a housing configured for insertion in a mammalian gastrointestinal (GI) tract;
a plurality of sensors including:
    a first sensor comprising at least one radiation emitter arranged to emit radiation to the environment outside the housing and a radiation detector arranged to detect radiation from the environment
    at least one additional sensor for detection of a condition in the environment,
a drive circuit for controlling the sensors, and
a data transmitter for transmission of detection data received by the plurality of sensors.

In some examples, the housing has at least one portion which is transparent to sensing radiation, and the first sensor is arranged to emit radiation through the housing to the environment outside the housing and to detect radiation from the environment through the transparent portion of the housing. In some examples, the drive circuit is configured to activate the sensors with time separation to prevent interference.

In some examples, the first sensor is arranged to emit radiation into a sensing volume formed by a recess of the housing, the sensing volume being open to access by fluids in said environment.

In some examples, the housing forms a plurality of sensing volumes, and there is an associated first sensor radiation emitter and radiation detector pair for each said sensing volume.

In some examples, the housing forms at least one sensing volume facing longitudinally and at least one other sensing volume facing laterally away from said longitudinal axis. In some examples, the at least one additional sensor comprises an electrical pH sensor providing as pH detection data. In some examples, the at least one additional sensor comprises at least one pressure sensor. In some examples, at least one pressure sensor comprises a diaphragm having an external surface, wherein deflection of said diaphragm indicating local pressure.

In some examples, there are a plurality of pressure sensors each mounted in a longitudinal direction to face radially, and they are preferably arranged circumferentially around the housing. In some examples, the pressure sensor is mounted in a narrowed portion of the housing.

In some examples, the at least one additional sensor comprises a camera sensor. In some examples, the camera sensor is mounted to face longitudinally. In some examples, the camera sensor is arranged to provide a video sequence with a time frame. In some examples, the biosensor is configured for moving with a particular orientation in the GI tract.

In some examples, the biosensor comprises a power source battery which is located at one end of the housing in the longitudinal direction, the battery having a weight to bias movement of the housing in said longitudinal direction.

In some examples, the biosensor further comprises a retainer for retention of the housing at a particular location in the GI tract for a period of time.

In some examples, the retainer comprises a biodegradable suture for time-limited retention, and optionally the suture is configured for retention for a period in the range of 2 to 20 days, preferably 3 to 7 days. In some examples, the retainer comprises an adhesive for engagement with the wall of the GI tract. In some examples, the adhesive is surrounded by a sacrificial layer which exposes the adhesive after a period of time. In some examples, the retainer comprises a magnetic element for operating in conjunction with an external magnet.

In some examples, the biosensor comprises a buoyant element mounted to an external surface of the housing to bias it to an orientation with sensors immersed in liquid. In some examples, the buoyant element surrounds the housing in the longitudinal direction.

In some examples, the sensing volume recess is formed by a housing base wall, and first and second walls substantially facing each other for passage of radiation for absorption detection of material within the sensing volume. In some examples, the housing forms a convex lens for passage of radiation into the sensing volume, and a concave lens for passage of radiation into the detector. In some examples, the housing has a dimension in the direction between the opposed walls of the sensing volume in the range of 2 mm to 7 mm.

In some examples, the transmitter includes an antenna which is optionally mounted in a domed end of the housing and is optionally in the form of a spiral with decreasing diameter in a direction towards an end of the housing. In some examples, the antenna has a maximum radial dimension in the range of 7.5 mm to 9 mm and it narrows to form an apex with a radial dimension in the range of 2 mm to 4 mm. In some examples, the transmitter comprises RF circuits located adjacent to the antenna, on a substrate extending longitudinally.

In some examples, the biosensor comprises a power management circuit board mounted transversely across the housing and defining a space for a battery compartment. In some examples, the first sensor comprises one or more LEDs and one or more photodetectors, and the transmitter is configured to provide a plurality of readings for a particular radiation wavelength and to eliminate outliers and to average non-outlier readings.

In some examples, the first sensor comprises a plurality of optical emitter devices each adapted to emit at a particular wavelength and the drive circuit is configured to activate each emitter device according to a time multiplex scheme, and optionally the time separation between activations is in the range of 2 ms to 5 ms. In some examples, the biosensor includes a light-absorbing guide surrounding a path between the radiation emitter and/or detector of said first sensor and the housing. The guide may advantageously comprise a substantially black material and/or an optic fibre.

In various aspects we also describe a biosensor system comprising a biosensor of any example and a processor linked with the sensors for processing the detection data in combination to provide information about said biosensor environment.

In some examples, the processor is wirelessly linked with the transmitter.

In some examples, the system comprises a catheter and a plurality of housings and sensors mounted along the length of the catheter. The capsules may be linked with the processor by wire along the catheter.

In some examples, the at least one additional sensor comprises an electrical pH sensor that provides pH detection data, and the processor is configured to estimate location of the biosensor housing in the GI tract in use according to the pH data detection data.

In some examples, the at least one additional sensor comprises at least one pressure sensor to provide pressure detection data, and the processor is configured to estimate location in the GI tract according to pressure detection data.

In some examples, a sensor comprises a camera and the camera is arranged to provide a video sequence with a time frame and processor is configured to embed data derived from the first sensor into a camera video stream timeline.

In some examples, the processor is configured to determine an indication of presence of a particular fluid according to a ratio of detected signal of said first sensor for one emitter wavelength to that of another emitter wavelength. In some examples, there is a particular ratio threshold for each of a plurality of combinations of radiation wavelengths. In some examples, the combinations include one or more of: red: green, far red:green, red:blue, far red:blue, far red:red.

In some examples, the processor is configured to determine from said first sensor an indication of presence of a particular fluid according to determining an angle as an arctan of a wavelength difference divided by a difference in detected signal and comparing said determined angle with a threshold angle.

In some examples, the processor is configured to determine from said first sensor detection data a severity value for an indication of presence of a particular fluid according to detected signal amplitude for one or more radiation wavelengths. Preferably, the severity value is an indicator of extent of internal bleeding.

In some examples, the processor is configured to, using detection data from said first sensor, determine a proportion of fall in detected signal strength for one or more emitter wavelengths as a parameter in determining the severity value.

In some examples, the processor is configured to use different light wavelengths to distinguish new blood from old blood. In some examples, the processor is configured to use a ratio of two wavelengths to indicate old blood and a ratio of different wavelengths to indicate fresh blood. In some examples, the processor is configured to use a ratio of Far Red/Red (FR/R) to indicate old blood and a ratio of Far Red/Green (FR/G) for fresh blood.

In some examples, the processor is configured to use detection data from an additional sensor to select an algorithm to calculate blood concentration.

In some examples, the processor is configured to use pressure sensor detection data to estimate the extent of liquid surrounding the biosensor. In some examples, the processor is configured to use pressure detection data in combination with first sensor detection data to determine if the biosensor is lodged in the GI tract with a sensing channel obstructed, and/or if the biosensor is going through a valve.

In some examples, the processor is configured to process detection data from the first sensor and from a pH sensor to generate data concerning what radiation sensor wavelength to activate.

In some examples, the processor is configured to use a pH-specific algorithm to calculate blood concentration. In some examples, the processor is configured to select a blood concentration on the basis that a ratio of Red transmitted light to orange transmitted light in the range of 1 to 1.5 indicates a low concentration of blood, while a value in a range of 2 to 10 indicates a medium concentration of blood, and a value greater than 10 indicate a high concentration of blood.

In some examples, the processor is configured to process detection data from a pressure sensor to determine how much liquid is surrounding the biosensor. In some examples, the processor is configured to use detection data from a pressure sensor and/or from a pH sensor to estimate orientation of the biosensor with respect to the GI tract.

In some examples, the processor is configured to determine whether there is enough liquid around the biosensor, and/or whether the biosensor is lodged in the GI tract, and/or whether a first sensor sensing channel is being obstructed, and/or if the capsule is going through a valve, and/or whether there is higher risk of misdiagnosis.

In some examples, the processor is configured to monitor images for a camera sensor and to activate the first sensor to analyse a radiation spectrum to check if fluid is blood, gastric fluid, and/or other pancreatic enzymes, and/or bile.

In various examples, the biosensor comprises two or more of radiation, pH, temperature, image, and pressure sensors, and the processor is configured to use detection data from at least two of said sensors to provide any one or more of the following outputs:

biosensor location, for example using pH detection data;

determination as to whether detected blood is fresh or old blood;

concentration of fluid around the capsule;

information on biosensor transit and location, for example using pressure detection data;

whether the biosensor is in liquid;

determination of validity of data collected by the radiation sensor;

determination if the capsule is lodged in the GI tract, for example using temperature data, and temperature changes may indicate if the capsule has left the body;

a command for activation of the camera based on detection data from a sensor other than the camera, for example to capture a video stream for a particular part of the GI tract according to pH data and/or pressure profile data;

a command for activating the camera for spectro-analysis to verify the presence of blood or bile; and/or a command for activating the camera to take video or still images of a region.

In various aspects we describe methods of operation of a biosensor system of any example, comprising the processor processing the detection data in combination to provide information about said biosensor environment.

In some examples, the at least one additional sensor comprises an electrical pH sensor providing pH detection data, and the processor estimates location of the biosensor housing in the GI tract in use according to the pH detection data.

In some examples, the at least one additional sensor comprises at least one pressure sensor to provide pressure detection data, and the processor estimates location in the GI tract according to pressure detection data.

In some examples, the biosensor comprises a camera sensor which provides a video sequence with a time frame, and processor embeds data derived from the first sensor into a camera video stream timeline.

In some examples, the processor determines an indication of presence of a particular fluid according to a ratio of detected signal of said first sensor for one emitter wavelength to that of another emitter wavelength.

In some examples, the processor uses detection data from an additional sensor to select an algorithm to calculate blood concentration. In some examples, the processor uses pressure sensor detection data to estimate the extent of liquid surrounding the biosensor.

In some examples, the processor uses pressure detection data in combination with first sensor detection data to determine if the biosensor is a lodged in the GI tract with a sensing channel obstructed, if the biosensor is going through a valve.

In some examples, the processor processes detection data from the first sensor and from a pH sensor to generate data concerning what radiation sensor wavelength to activate.

In some examples, the processor uses a pH-specific algorithm to calculate blood concentration.

In some examples, the processor selects a blood concentration on the basis that a ratio of Red transmitted light to orange transmitted light in the range of 1 to 1.5 indicates a low concentration of blood, while a value in a range of 2 to 10 indicates a medium concentration of blood, and a value greater than 10 indicate a high concentration of blood.

In some examples, the processor processes detection data from a pressure sensor to determine how much liquid is surrounding the biosensor.

In some examples, the processor uses detection data from a pressure sensor and/or from a pH sensor to estimate orientation of the biosensor with respect to the GI tract.

In some examples, the processor determines whether there is enough liquid around the biosensor, and/or whether the biosensor is lodged in the GI tract, and/or whether a first sensor sensing channel is being obstructed, and/or if the capsule is going through a valve, and/or whether there is higher risk of misdiagnosis.

In some examples, the processor monitors images from a camera sensor and activates the first sensor to analyse a radiation spectrum to check if fluid is blood, gastric fluid, and/or other pancreatic enzymes, and/or bile.

In various examples, the biosensor comprises two or more of radiation, pH, temperature, image, and pressure sensors, and the processor uses detection data from at least two of said sensors to provide any one or more of the following outputs:

biosensor location, for example using pH detection data;
  determination as to whether detected blood is fresh or old blood;
  concentration of fluid around the capsule;
  information on biosensor transit and location, for example using pressure detection data;
  whether the biosensor is in liquid;
  determination of validity of data collected by the radiation sensor;
  determination if the capsule is lodged in the GI tract, for example using temperature data, and temperature changes may indicate if the capsule has left the body;
  a command for activation of the camera based on detection data from a sensor other than the camera, for example to capture a video stream for a particular part of the GI tract according to pH data and/or pressure profile data;
  a command for activating the camera for spectro-analysis to verify the presence of blood or bile; and/or
  a command for activating the camera to take video or still images of a region.

Definitions

To facilitate the understanding of this invention, a number of terms are defined below. Terms defined herein have meanings as commonly understood by a person of ordinary skill in the areas relevant to the invention. Terms such as "a", "an", and "the" are not intended to refer to only a singular entity but include the general class of which a specific example can be used for illustration. The terminology herein is used to describe specific embodiments of the invention, but their usage does not limit the invention, except as outlined in the claims.

As used herein, the term "sensing volume" refers to a space, internal or external, into which liquid may flow for sensing (e.g., sensing, e.g., by any sensor described herein). A sensing volume may be defined by the housing of the capsule, e.g., be, or be within, a "recess" of the housing of the capsule.

As used herein, the term "biosensor" refers to a sensor for biological, clinical, or medical purposes, but may be used interchangeably with the words "sensor" or "capsule" herein.

As used herein, the term "capsule" refers to a device which can pass through the GI tract, such as by being ingested, delivered in the GI tract using endoscopic means, or could be placed during surgery, for example through a laparoscopic channel.

As used herein, the term "substrate" refers to an underlying surface or feature, for example such as a mount for an electrical component, etc.

As used herein, the term "recess" refers to a hollow feature.

As used herein, the term "noise" refers to unwanted disturbances in a measured or transmitted signal.

As used herein, the term "old blood" refers to blood which was bled before detection, for example between 1 and 24 hours, or more, before detection. "Old blood" may be more brown in colour as compared to "new blood."

As used herein, the term "new blood" refers to blood resulting from active bleeds, or recently bled (e.g., within one hour) at the time of detection. New blood may be more red in colour as compared to "old blood."

As used herein, the term "belt" refers to an element that sits around a device or system, for example the buoyancy belt or magnetic retention belt discussed below.

As used herein, the term "deflection" refers to displacement from a plane at which a surface sits at rest (e.g., bending, depressing, expanding, etc).

As used herein, the term "housing" refers to, and may be used interchangeably with, a covering, casing, or enclosure.

As used herein, the term "retention" refers to securement, such as a capsule ability to retain to a GI tract wall.

As used herein, the term "sacrificial" refers to a material that is designed to be used, decayed, degraded, or destroyed to fulfil a function.

As used herein, the term "domed" refers to a rounded or convex geometry on the capsule.

As used herein, the term "obstruction" refers to matter, such as that within in the GI tract, which may "obstruct" or block sensing volumes or passageways on the capsule, or obscure the operation of sensors.

As used herein, the term "lodged" refers to an instance in which a capsule may become caught or fixed in the GI tract.

As used herein, the term "photo-detector" refers to an element that responds to photonic stimuli to produce or change an electrical signal.

BRIEF DESCRIPTION OF THE DRAWINGS

The invention will be more clearly understood from the following description of some embodiments thereof, given by way of example only with reference to the accompanying drawings in which:

FIG. 5 is a pair of perspective views of a capsule with pH sensors at one end, FIG. 6 shows the main components for processing pH data, and FIG. 7 is a plot showing pH outputs;

DETAILED DESCRIPTION OF THE INVENTION

The following description is of various examples of the invention, and specific details in the description and drawings are not to be interpreted as limiting of the scope of the invention.

The present invention features devices, systems, and methods for use thereof for detecting conditions in the gastrointestinal (GI) tract. The devices and systems described herein can be used for a variety of purposes, including monitoring of blood presence in the GI tract. The devices and systems described herein may comprise one or more sensors, such as pressure sensors, pH sensors, temperature sensors, optical sensors, etc.

Figures 1, 2, 3, 4:
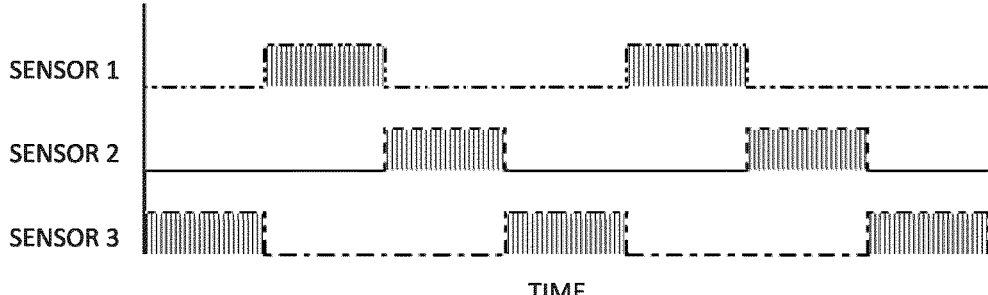
FIG. 1 is a perspective exploded view of a biosensor capsule of the invention.
FIGS. 2 and 3 show alternatives with different external sensing volumes which are outside the housing but within recesses formed by the housing.
FIG. 4 is a set of plots showing sequencing of sensor operations to avoid interference.

Referring to FIG. 1 a biosensor in one example comprises a capsule 1 having a housing formed by two moulded housing halves 2 and 3, enclosing an assembly 4 with a battery 5, an antenna 7, a transverse sensor circuit substrate 8, a longitudinal sensor circuit substrate 9, and another transverse substrate 10 linked with the batteries 5. The sensor 1 communicates wirelessly via the antenna 7 with a separate receiver. A light shield 6 of planar construction is also part of the assembly. The housing has internal features 20 for clipping to the substrate 9.

The capsule 1 is also configured to enable data collection and wireless transmission to an external receiver with a communication assembly, a processor, and a user interface which also form part of the sensing system. There may also be data processing and/or storage within a cloud-based server.

The invention may provide just a set of one or more biosensors with a capacity to communicate with a third party receiver, or a biosensor system with a set of one or more biosensor capsules and a host with a receiver configured to receive data from the capsules(s) and to process it to provide useful data for medical analysis.

The biosensor capsule is configured to monitor conditions, and detect anomalies, within hollow organs of a patient. In one embodiment, the biosensor capsule 1 is configured to identify blood within the GI tract of the patient. The identified blood includes blood that may be accumulated in the stomach of a patient for 1 to 24 hours, and is not actively bleeding at the time of ingestion ("old blood"). The capsule also identifies the presence of on-going active bleeding in the stomach at the time of monitoring. The capsule 1 is configured to distinguish between "old blood" and "active bleeding".

As shown in FIG. 1, the capsule may have a generally cylindrical shape with first and second domed ends, and an external sensing volume formed by a recess 11 in the housing ⅔ between the domed ends. The recess 11 provides a sensing volume formed by three planar walls 12, 13, and 14 of the housing part 2. The walls 13 and 14 are transparent to radiation sensor sensing wavelengths (for example, visible light radiation) of interest, and they face in the longitudinal direction. A base of the recess 11 is formed by the wall 12. As described in more detail below, the walls 13 and 14 may act as lenses for passage of light in the longitudinal direction for absorption detection of material within the sensing volume of recess 11. As described in more detail below, in other embodiments the components of the capsule may be arranged for fluorescein detection in addition to light absorption, and also other forms of sensing such as pH and pressure.

The materials and geometry of the capsule have been selected to increase the flow of the gastric liquids toward the sensing volume of recess 11 of the capsule and reduce the risk of obstruction from food and other particles. This may be achieved for example by the physical arrangement of the volume, such as it being shallow (2 mm to 5 mm) and/or having splayed side walls. In some instances, a smaller overall size of the biosensor may aid in, for example, ingestion of the biosensor. The manner in which the components are mounted within the enclosure is very advantageous in minimizing volume of the biosensor. Alternatively, larger volumes may be advantageous for other applications of the biosensor.

An assembly 4 of components of the capsule 1 comprises a light-emitting diode (LED) light source on the substrate 10 and aligned in the longitudinal direction with an absorption photodetector on the substrate 8. The substrate 9 is for a processor and associated components, and it extends in the longitudinal direction substantially parallel to the base wall 12. The substrate 9 is linked by flexible cables to the orthogonal emitter (circuit board) substrate 10 which supports the light source LED and associated components and to the detector substrate 8. The substrates 8, 9, and 10 are printed circuit boards (PCBs) with conductive tracks and supporting the components. There is also a power supply circuit board 15 in the domed end opposed to that of the antenna 7, and with components including a magnetic switch, a boost converter and associated components. The substrate 15 is spaced apart from the substrate 10, defining a space between for batteries 5. The substrate 10 is linked to the substrate 15 by a semi-flex PCB 16.

The arrangement of the substrate 9 being longitudinal and the substrates 8 and 10 being transverse and orthogonal may allow an advantageous fitting of components, including the relatively large microcontroller in the space between the substrate 9 and the opposed housing part 3 wall. In one embodiment, the arrangement may provide for an optimal use of space to accommodate the batteries 5 and associated power components 15. Strategic arrangement of components may allow for different size biosensors. For example, the configuration seen in FIG. 1 may help to ensure that the capsule is not excessively large, while having enough power for a sensing duration greater than 3 days. However, capsule size is not directly correlated to battery power.

Also, the substrate 9 may have notches on one side for test probe access to pins of the microcontroller to allow programming of the microcontroller. This component provides the local, onboard control functions, including providing drive signals for the sensors and initial signal processing of detection data from the sensors. However, in several embodiments, the main processing of the detection data may be performed by an external processor also forming part of the biosensor system.

In various examples the substrates 8, 9, and 10 support multiple sensors, and in other examples there may be additional substrates for sensors. As is described in more detail below, the sensors may include at least one first sensor which is based on radiation emission and sensing, one example of the radiation being light emitted by light emitting diodes (LEDs) and detected by photodetectors (PDs). They also may include at least one additional sensor. The plurality of sensors enables the onboard processor and/or the processor in the external receiver to receive multiple feeds and perform algorithmic processing to combine the data to provide significant patient GI tract information for medical personnel. For example, the sensed parameter values may be used in combination to determine the location of the sensor.

The biosensor capsule 1 may be configured to be ingested and to measure and monitor the presence of gastric fluids, bile and bile containing pancreatic enzymes. There may be blood within the gastrointestinal (GI) tract, and this is detected by the capsule. In one embodiment, the capsule may be activated when desired by wireless control signals from the host after ingestion. The capsule 1 may also be activated prior to ingestion. The capsule 1 may also be configured to enable data collection onboard and wireless transmission to a receiver which also forms part of the sensing system. The extent of onboard data storage is chosen to suit the application. In general, it is preferred that there is both onboard data storage and also real time transmission for external storage and processing, to allow real time monitoring and also reduce risk of data loss.

In a preferred embodiment, the capsule 1 is configured to identify blood within the GI tract of the patient, including distinguishing between blood accumulated in the stomach of a patient for hours and not actively bleeding at the time of ingestion ("old blood"), and active bleeding at the time of ingestion ("new blood").

The physical arrangement of the housing may be different from than illustrated in FIG. 1, in order to accommodate different sensor arrangements. Indeed, the housing may not be of a rigid material, and it is envisaged that it may be at least partially of a softer material, for example such as a flexible polymer or gelatine. The generally cylindrical shape with first and second domed ends and a recess 11 between the domed ends and facing laterally is particularly advantageous for optical radiation sensing and, if desired, fluorescent sensing. The walls for sensor radiation transparency may be shaped for optimal direction of the radiation, such as forming a convex shape facing a light emitting diode (LED) and forming a concave shape facing a photodetector (PD). For example, for fluorescence sensing, the best approach to lensing is to diffuse the light as much as possible to excite the surrounding area and then to focus the emitted fluorescence light towards the photodetector. For absorbance measurement the same approach may work but depending on the component arrangement also focusing both light from LED and light towards the PD might be advantageous for focus on a known space.

Any or all of the transparent walls may form lenses for passage of radiation with desired directionality according to the type and location of the emitters and receivers. While the transparent walls are mutually orthogonal in some embodiments, they may be arranged with mutual angles other than 900 for example an angle in the range of 750 to 105°, for optimising sensing performance, and to be splayed to reduce risk of food being lodged. The distance between the walls 13 and 14 may be 4.0 mm or in other examples 4.5 mm. The thickness of the walls is preferably in the range of 0.7 mm to 0.9 mm, and more preferably about 0.8 mm, in order to minimise refraction and magnification, and more generally is preferably in the range of 2 mm to 7 mm. The walls facing each other across a sensing volume formed by a recess may in various embodiments have an angle with respect to the longitudinal axis ranging from 90° to 150°, and in this embodiment the walls 13 and 14 are at 90°+draft angle, to facilitate content to be analysed.

In certain embodiments, the dimensions of the capsule are: length: 27 mm, preferably in the range of 15 mm to 30 mm; diameter: 11 mm, preferably in the range of 5 mm to 12 mm.

The transparent walls are, in various embodiments, of polycarbonate, PMMA, Polyethylene Terephthalate (PET), Amorphous Copolyester (PETG), Polyvinyl Chloride (PVC), Liquid Silicone Rubber (LSR), Cyclic Olefin Copolymers, Polyethylene (PE), Transparent Polypropylene (PP), Styrene Methyl Methacrylate (SMMA), Polystyrene, MABS (Transparent modified ABS).

As noted above, the assembly 4 comprises an LED light source aligned in the longitudinal direction behind the wall 13 with an absorption photodetector (PD) on the opposed side of the sensing volume of recess 11 and behind the opposed wall 14. The sensors and control components are mounted on any desired combination of the substrates 8, 9, and 10, and the processor (in this case a microcontroller) is between the substrate 9 and the housing curved wall. Internal flexible cables may link the substrates, in certain embodiments.

Antenna

Reliable transmission and reception of wireless data and control signals is important. In one embodiment, there is preferably an antenna in the capsule. The antenna may, for example, be integrated into the housing, but for example may be conductors wound around it in either or both longitudinal or transverse directions. In FIG. 1, the antenna is a discrete component mounted into one of the domed ends, and this is particularly advantageous for capsule sizing, for example.

In FIG. 1, the antenna 7 is shown to have a spiral shape with decreasing diameter to form a conical shape with an apex towards the end of the housing. It has nine full circular turns, the largest of which has diameter of 8.6 mm in this example. The antenna may be made of enamelled copper with a diameter of 0.35 mm. The antenna parameters are preferably within the ranges of: maximum diameter: 7.5 mm to 9 mm; apex-end diameter: 2 mm to 4 mm; number of turns: 7 to 10; taper angle: 60° to 80°; thickness of the wire: 0.2 mm to 0.5 mm; material: enamelled copper, but in other embodiments it could for example be silver, aluminium, or stainless steel.

The antenna may, in other examples, be encapsulated in a coating, such as one or more selected from epoxy polyurethane, parylene and benzo-cyclo-butene (BCB), polytetrafluoroethylene (PTFE), perfluoroalkoxy alkanes (PFA) and fluorinated ethylene propylene (FEP).

In FIG. 1, the antenna is placed at one end of the capsule, at a minimum of, for example, 5 mm from the batteries. Its shape as shown in FIG. 1 is designed also to maximise the volume available within the capsule. The microcontroller on the substrate 9 is physically close to the antenna 7, with a radio-frequency (RF) tuning component. The microcontroller also has the following functional blocks in this example: filter signal conditioning linked to a photodetector; an analog-to-digital converter (ADC), in turn linked to storage; an encode function; an RF circuit; a control block that controls the regulation circuit, which is linked to a power management block.

Radiation Sensors

One example of the first radiation sensor is an optical sensor in which the radiation is visible light. The optical sensor may include an LED light source and associated photodetector. The light source in one example emits light at different wavelengths within the visible spectrum, including a violet light, a blue light, a green light, a yellow light, an orange light and a red light. Each substance of blood has its own light absorption profile and the wavelengths are selected to amplify irregular characteristics of the blood absorption spectrum. The photodetector may cover the whole visible spectrum, detecting the light and transmitting it to the amplifier, which collects and transforms photons into voltage/current and then converts it into a digital signal.

In various examples the optical sensor comprises a singular light source or an array of multiple light sources, similarly the photodetector may comprise a singular photodetector device or an array of multiple devices. In some examples, a single light source emits light at any of four wavelengths within the range 300 nm to 900 nm, and the photodetector is configured to cover this whole spectrum. The microcontroller activates the LEDs to enhance optical performance while limiting power consumption, and is configured to pulse the LEDs and other sensors sequentially, for emission at its particular wavelength, and short pulses may be preferable to optimise battery. It will be appreciated that some or all of the components can be integrated into the capsule, such as the photodetector, amplification, microcontroller and RF module. The individual wavelengths may be activated with a time delay (of for example 2 ms to 20 ms, e.g., 8 ms) in-between, hence operating a form of time-division multiplexing on the channel between the walls.

The following is one embodiment of a sequence for operation of the optical sensor:

The microcontroller enables LED1 (=LED1 is on). The microcontroller also enables the photodetector and takes 10-30 measurements from the photodetector.

The photodetector sends 10 to 30 voltage signals to the ADC of the microcontroller. The microcontroller is programmed to eliminate the higher and the lower values and it averages the remaining values. The resulting averaged number VLED1 is a voltage which is proportional to the absorbed light received by the photo detector while LED1 is on. LED1 is switched off after about 2 ms to 5 ms.

LED2 is now turned on. The photodetector measures the VLED2. LED2 is tuned off after 2 to 5 ms. This sequence is repeated for each LED. When all of the LEDs have been pulsed and all of the VLEDn (voltage levels of signals for the relevant wavelength of emission) have been recorded, all LEDs are switched off and the photodetector takes the latest set of measurements when no light sources are active.

The VLED_OFF is a sign of possible ambient or environment light and it is then used to eliminate possible light background noise.

At this point, the photodetector is also switched off until a new set of measurements have to be made. The frequency of measurement is programmed based on the clinical conditions. A slow frequency (e.g., every 1-2 minutes) is implemented when the results show that the risk of bleeding is low. As soon as the system detects the possibility of a bleed, the frequency can be automatically updated for more comprehensive monitoring (e.g., every 2 seconds).

The data can be used to detect the presence of blood in a manner which is instantaneous. For example:

If $LED1 = RED$ light $(620 - 700$ nm$)$, $LED2 =$ $$\text{Far\_Red } (700 - 750 \text{ nm}); LED3 =$$

$$\text{Green light } (495 - 570) \text{ and } LED4 = \text{Blue light } (450 - 495),$$

we have the following conditions to estimate the presence of blood:

$$\text{If } V_{RED}/V_{GREEN} = R_1 > \text{threshold1} \rightarrow \text{BLOOD}$$

$$\text{OR if } V_{FAR\_RED}/V_{GREEN} = R_2 > \text{threshold2} \rightarrow \text{BLOOD}$$

$$\text{OR if } V_{RED}/V_{BLUE} = R_3 > \text{threshold3} \rightarrow \text{BLOOD}$$

$$\text{OR if } V_{FAR\_RED}/V_{BLUE} = R_4 > \text{threshold4} \rightarrow \text{BLOOD}$$

$$\text{OR If } V_{FAR\_RED}/V_{RED} = R_5 > \text{threshold5} \rightarrow \text{BLOOD}$$

$$\text{OR } V_{RED} \& V_{GREEN} \& V_{BLUE} < \text{threshold6} \rightarrow \text{BLOOD}$$

$$\text{OR } V_{RED} \& V_{FAR\_RED} \& V_{GREEN} \& V_{BLUE} < \text{threshold7} \rightarrow \text{BLOOD}$$

$$\text{OR } \arctan(\lambda_{GREEN} - \lambda_{BLUE})/(V_{GREEN} - V_{BLUE}) =$$

$$\Theta_1 > \Theta_{THRESHOLD1} \rightarrow \text{blood}$$

US 12,697,044 B2

13

-continued $$\text{OR } \arctan(\lambda_{RED} - \lambda_{GREEN})/(V_{RED} - V_{GREEN}) = \Theta_2 > \Theta_{THRESHOLD2} \rightarrow \text{blood}$$

$$\text{OR } \arctan(\lambda_{FAR\_RED} - \lambda_{RED})/(V_{FAR\_RED} - V_{RED}) =$$

$$\Theta_3 > \Theta_{THRESHOLD3} \rightarrow \text{blood} \quad 5$$

where all of the threshold values are values within an arbitrary unit range such as 1.8 to 2.2; threshold values are values within the range 0 to 300 mV, and $\Theta_{THRESHOLD\ 1}$, $\Theta_{THRESHOLD\ 2}$, $\Theta_{THRESHOLD\ 3}$ are angles within the range 0° to 70°. In the above, $\lambda_{GREEN}$, $\Theta_{BLUE}$, $\Theta_{RED}$, $\Theta_{FAR\_RED}$ are the wavelengths for these colours, for example for green it is preferably between 560-520 nm.

If blood has been detected using one or multiple conditions stated above, it is possible to identify a severity index (SI) of the bleed. The severity index (SI) is calculated as the percentage drop of $V_{RED}$ and/or $V_{GREEN}$ at a certain time compared to base initial values of $V_{RED}$ and/or $V_{GREEN}$, when there is no blood. At higher concentrations of blood, the absorption of red and/or green light is higher and therefore the current, or related voltage, emitted by the photodetector 22 decreases.

Optical Sensor Detection of Old vs. New Blood

The system can use different light to detect new blood (vivid red blood colour) from the old blood (which has a brown component due to oxidation of haemoglobin). For example, the processor can use FR/R for old blood and FR/G for fresh blood. By using at least four wavelengths more accurate information is provided, akin to a discrete spectrophotometer. Blood at high concentrations also absorbs the Red light, so the presence of blood cannot depend uniquely from the ratio; absolute values may also be considered. Also, by considering the absolute values of some wavelengths (for example the green light absorption), the algorithm can correlate to the blood concentration.

In another embodiment, each light source has a specific wavelength and also a specific optical power that can be regulated by the microcontroller. The microcontroller can increase or decrease the activation time of each LED resulting in a chosen light intensity.

Resistors may be used to regulate the output light intensity. The circuit may be configured with components such as a voltage-controlled resistor (e.g., an N-MOSFET). In this case, an optical sensor photodiode may be provided to feed the information back to the microcontroller 6 in order to continuously adjust the output. For example, there may be one target for a stationary capsule, and a different one for travel through the GI tract.

Using any of these mechanisms the microcontroller can implement a specific intensity for each LED in order to control the required optical power output. It will be appreciated that the processor provides full results by instantaneous measurements as described above, based on combinations of wavelengths. The Severity index (SI) is determined as the percentage drop of one single light wavelength from the expected "no blood condition" light wavelength.

In various examples there may be a source with a single broadband LED and multiple filtering lenses each providing an associated wavelength, in one example green (G), blue (B), Red®, and Far Red (FR). There may be an array of discrete LEDs each providing a specific wavelength. There may be the broadband photodetector 300; and/or multiple discrete photodetectors; and/or one component with multiple sensitive areas, each sensitive to a specific wavelength; and/or an assembly of a broadband photodetector (PD) with a detachable cover to filter selectively. Light sources, photodetectors and optical components (for example filters, collimators and fibre optics) may be assembled in order to ensure both absorbance and fluorescence detection. The distance and angle of the components in relation to each other is selected to ensure performance of sensors while minimizing volume and weight of components, as well as the capsule as a whole.

The above examples are emitters and detectors using visible light radiation. However, components for other type of radiation may be used additionally or alternatively. Examples of alternative detectors include photomultipliers, CCDs, Solar cells, and phototransistors.

Radiation Blocking or Shielding

Radiation-blocking or shielding components may be used in the capsule for reduction of noise. Such components may be of a material including metal and/or plastics. A combination of material, colour and surface properties will be used for the shielding component.

In some examples the shielding component comprises black light-absorbing plastics material surrounding a path from a light emitter to a housing wall (e.g., walls 12, 13, 14, of capsule 1) and a path to a detector on the opposed side of the sensing volume. Each light absorber may form a light channel surrounded by light-absorbing material such as black plastics material or alternatively channeled within a fibre optic tube. Advantageously, the shielding components absorb light which is not close to the optical axis between the source and the detector. The light absorption helps to prevent radiation from scattering within the capsule and reaching the detector as noise. The prevention of noise can be aided also by a light shielding component adjacent the housing wall at the base of the sensing volume (e.g., of recess 11 of capsule 1). This embodiment of shielding material arrangement very effectively channels the light from the emitter into the photodetector, for both absorption and fluorescence modes of operation. For fluorescence, the light of the source reaches the sample medium to excite the fluorescence material and only the emitted light reaches the photodetector, the light coming from the source being noise.

Light absorbers can be provided as shielding components attached to the light emitter, or can be part of light emitter device packaging, or can be part of the capsule housing.

Additional Sensors

The present biosensor is advantageous in that it may comprise a plurality of sensors, with, for example, a first radiation sensor such as described above and one or more additional sensors. The additional sensors may in various examples include one or more of a fluorescent sensor, a pH sensor, a pressure sensor, a temperature sensor, etc. Additional sensors may be disposed about additional sensing volumes or may share a sensing volume. The onboard microcontroller and/or the processing in the external host may process the multiple streams of detection data to provide synergies in the extent of monitoring of conditions in the GI tract. Further details of additional sensors are given below.

Multiple Sensors, Locations

The arrangement as shown in FIG. 1 provides for the majority of the sensors to be facing longitudinally, however, other arrangements are possible. In these other arrangements some or all of the components of the assembly 4 are used, subject to change in their configuration according to location of the sensing volumes and their planar walls which may be transparent to sensing radiation.

Referring to FIG. 2 there is a sensing volume 101 and a sensing volume 102 at each end, providing longitudinally facing planar walls 103 and 104 respectively for sensor radiation.

As shown in FIG. 3, in a capsule sensor 200 there are longitudinally facing recess volumes 201 and 202 at opposed ends, and a laterally-facing sensing volume 203. There may be a different sensor for each sensing volume 201, 202, and 203, referred to as SENSOR 1, SENSOR 2, and SENSOR 3. The sensors may be activated individually in sequence as shown in FIG. 4, to avoid interference. Such sequencing may apply irrespective of the nature of the sensors and their locations.

The capsule may have one or multiple sensing volumes where the blood or other fluids can flow. For example, by having two sensing volumes on opposed sides with respect to a longitudinal axis, the capsule can sample the environment regardless of the capsule orientation. Any number or orientation of sensing volumes (e.g., recesses) are contemplated. Certain sensors may not require a sensing volume, e.g., pressure sensors.

Fluorescence Detector

An example of an additional sensor that may be used is a fluorescence detector, which is preferably mounted under a filter in contact with a wall 11, 12, or 13. Illumination to cause fluorescence is caused by operation of a visible light radiation emitter such as the LED on the substrate 10, causing fluorescence within the sensing volume of recess 11 during a time slot for emission of the relevant wavelength. The orientation of walls 13 and 14 is advantageous in that the light source and the detector may face each other for absorption-based measurements. In the embodiment shown in FIG. 1, the wall 12 is at 900 to the walls 13 and 14 for fluorescence measurements. The orientation of the walls may aid in minimizing the cross-talk between the fluorescence light source and the detector. The arrangement shown in FIG. 1, together with optical filters and collimators will ensure high-quality fluorescence measurements performance even in a miniaturised environment. Optical filters and collimator can be incorporated in the lens 3.

In the case where fluorophores such as the fluorescein (or for example, indocyanine green (ICG), methylene blue) are used, the fluorophores may be intravenously injected. In the case that the patient has an active upper gastrointestinal bleed, part of the fluorophore, such as fluorescein, will leak inside the stomach together with the blood. The fluorophore, such as fluorescein, reaches the stomach if internal bleeding is occurring, and then the system can identify active bleeding.

There may be at least one LED that emits the light within the excitation wavelength of the fluorophore, for example Fluorescein sodium, for which the wavelength is approximately 490 nm. A photodetector may comprise an optical filter to filter out all, or at least a portion of, the unwanted wavelengths except the light emitted from the excited fluorophore, e.g. Fluorescein sodium, for example approximately 520 nm. The light is converted into voltage by a light-to-voltage converter. Blood that leaks into the stomach brings with it the fluorophore, e.g., fluorescein, and the light produced by the excited fluorophore, e.g., fluorescein, is proportional to the amount of the fluorophore, e.g., fluorescein. Hence, the existence and severity of an internal bleed is detected. Fluorescein in particular is rapidly metabolised and it will become ineffective after 20 to 30 minutes and will no longer emit measurable fluorescence. The use of fluorescein, as well as other fluorophores, is a very effective mechanism to instantaneously detect active bleeding in real time. In some uses this mechanism may be in addition to or instead of the light detection methods described above. When the capsule is used it may be user-configured to use one or both mechanisms.

pH Sensors

At least one additional sensor may be an electrical pH sensor for gathering more information about the GI tract. Referring to FIG. 5, a capsule 300 may have a pair of pH sensors 301 at one end 302 and a longitudinally facing sensing volume 303 at the opposite end for optical sensing. As shown in FIG. 6, the pH sensor 301 may comprise electrodes 315 linked to a voltage buffer 310, an ADC 311, and a transmission circuit 312 linked with the microcontroller.

The pH measurement in the gastrointestinal tract varies as the capsule passes through the different sections of the tract, examples being given in the table below.

| Stomach | 1-3 |
|---|---|
| Duodenum | 6-7.4 |
| Small Intestine | 6-7.4 |
| Colon | 5.7-6.7 |

The pH sensor 301 comprises a measuring electrode and a reference electrode. If the probe is dipped into a test solution, the measurement electrode generates a voltage depending on the hydrogen ion activity. A typical output value is 59.14 mV per unit of pH at 25° C. Due to the temperature dependency, this value can rise to 70 mV/pH. This voltage is compared with that of the reference electrode. If the test solution is acidic (low pH), the potential at the probe output is greater than 0; for a basic solution, it is less than 0. The output value can be calculated using the following equation:

$$E_R = E_0 - \frac{2.303 \ RT}{nF}(pH - pH_{REF})$$

where:

E is the output voltage of the probe.

$E_0$ is the standard electrode potential (typically 0 V), dependent on the probe.

R is the universal gas constant. R=8.31447 J mol-1 K-1.

T is the temperature in Kelvin.

n is the number of transferred electrons (or equivalent number).

F is the Faraday constant. F=96485.34 C mol-1.

pH is the hydrogen ion concentration of unknown solution.

$pH_{REF}$=7, reference value of reference electrode.

The voltage buffer 310 may comprise an operational amplifier which is selected for, e.g., low power consumption, low noise, and extremely low input bias current. The full range of input to the ADC 311 is utilised by selection of the reference voltage. The circuit shown in FIG. 6 is advantageous as it is a simple, very precise, and power-saving variant for pH sensor readings. Once the circuit has been calibrated, an accuracy of +/−0.5%, corresponding to 0.005 units of pH can be achieved. FIG. 7 and the table above show how changes in pH can be used to determine the position of the capsule as it continues to detect blood.

The detection data from the pH sensor may be used by the processor to determine where the capsule is in the GI tract. It may alternatively or additionally be used by the processor in combination with first (optical) sensor detection data to discriminate fresh blood from new blood, and/or to provide blood concentration data.

Figure 16:
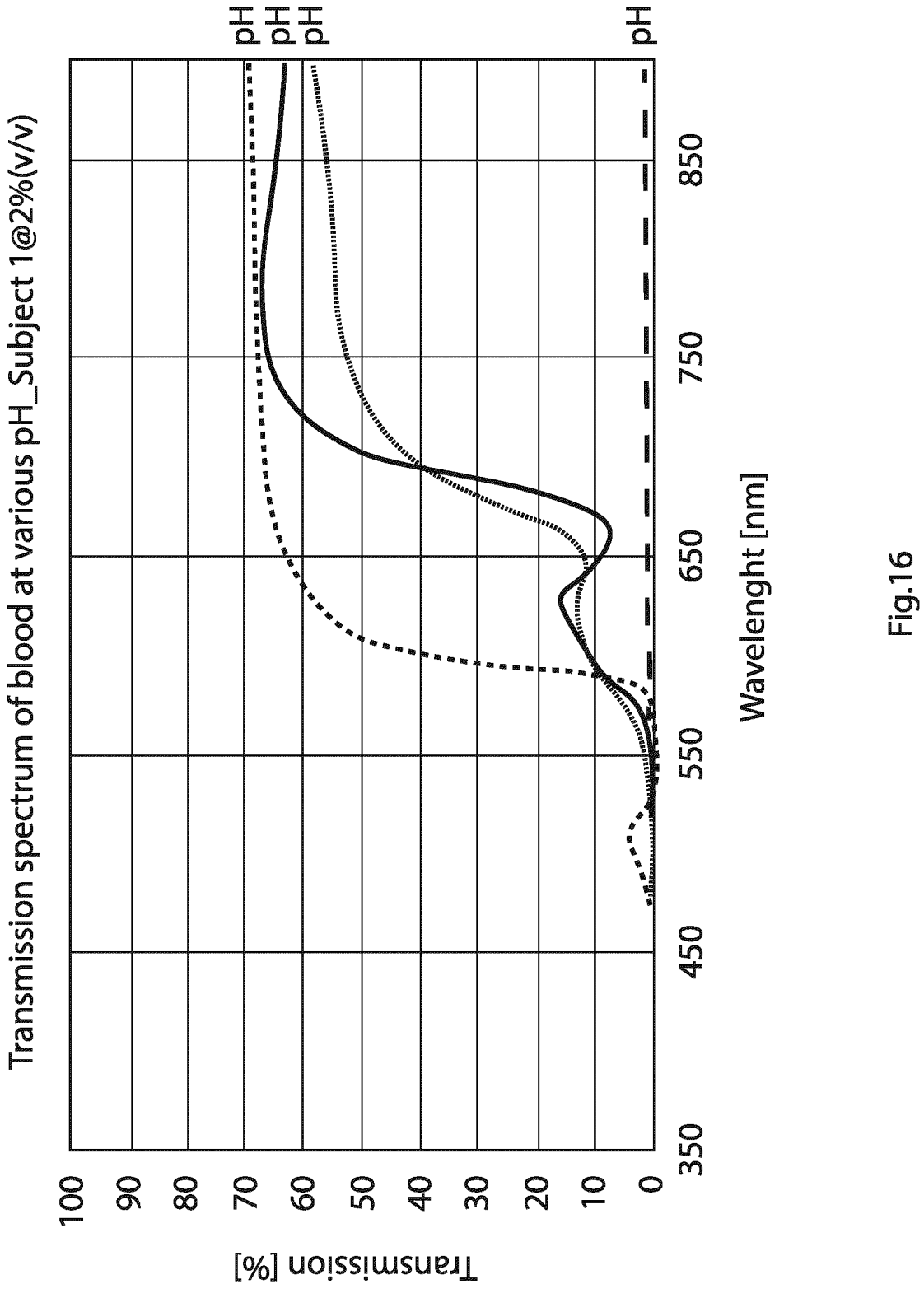
FIG. 16 is a spectrum derived from the light transmission analysis of blood at different pH values at a concentration of 2% (v/v)
Figure 17:
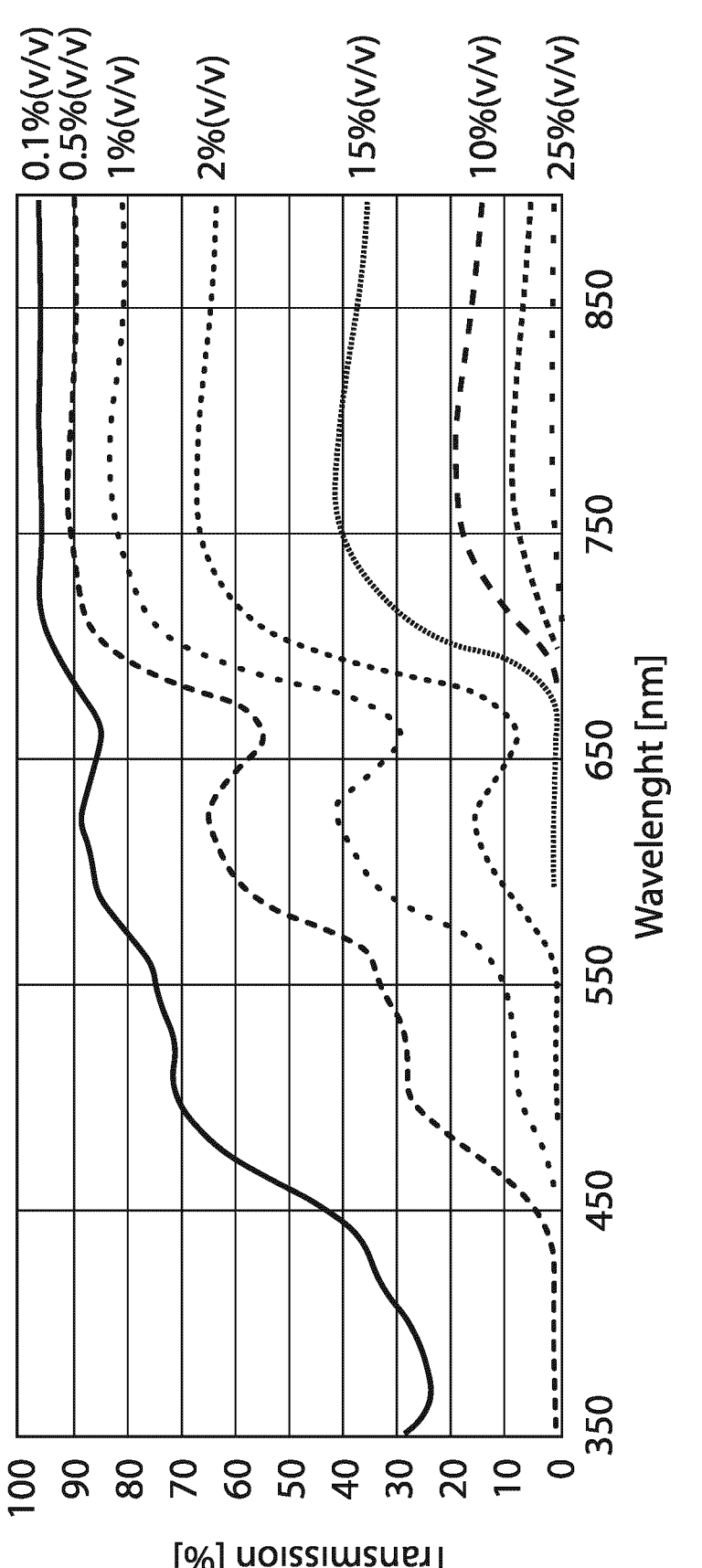
FIG. 17 is a spectrum derived from the light transmission analysis of blood at different concentrations with a pH value of 1.

The pH influences the absorption spectrum of blood. An example of how pH and concentration affect transmission spectrum of human blood is shown in FIG. 16, which shows transmission spectra of human blood at various pH, and FIG. 17 shows transmission spectra for various concentrations.

Detection data including outputs from the optical (LED) sensors and from a pH sensor may be processed to generate data concerning:

What radiation sensor wavelength to activate. For example, characteristic peaks at pH=7 are present around 500-510 nm and 750-760 nm. While at pH 1, wavelengths in the range of 610-630 nm and 750-760 nm are preferred (FIG. 16).

When knowing the pH, the processor might use a pH-specific algorithm to calculate blood concentration. For example, if pH=1 a ratio of Red transmitted light to orange transmitted light in the range of 1-1.5 indicates a low concentration of blood, while a value in a range of 2 to 10 indicates a medium concentration of blood and finally a value greater than 10 indicates a high concentration of blood.

Monitoring the evaluation of the blood concentration over time and/or the presence of old or active bleeding will inform on the health progress of the patient and evaluate if treatment shall be accelerated, if current proton pump inhibitor (PPI) treatment is adequate, etc.

Combination of data from radiation sensors and data from pH sensors can improve specificity compared to diagnoses made with the radiation sensors alone, e.g., an increase in specificity.

Pressure Sensors (FIGS. 8 to 11)

Pressure sensors may be provided in combination with other types of sensor described herein to obtain more detailed and useful information about conditions at the location of the capsule. A capsule of the invention may include one or more pressure sensors in combination with radiation and/or pH sensors, and/or any of the other sensors described herein.

Pressure sensors may be mounted to the external surface of the capsule housing, and this is preferably in a recessed part of the housing. The pressure sensors may face in any direction, but it is preferred that at least one faces laterally at an angle to the capsule longitudinal axis, such as 90° to the longitudinal axis. Pressure sensors may also be internal to the capsule. Pressure sensors may also face into a sensing volume. For example, to detect that a sensing volume is submerged.

Figure 8:
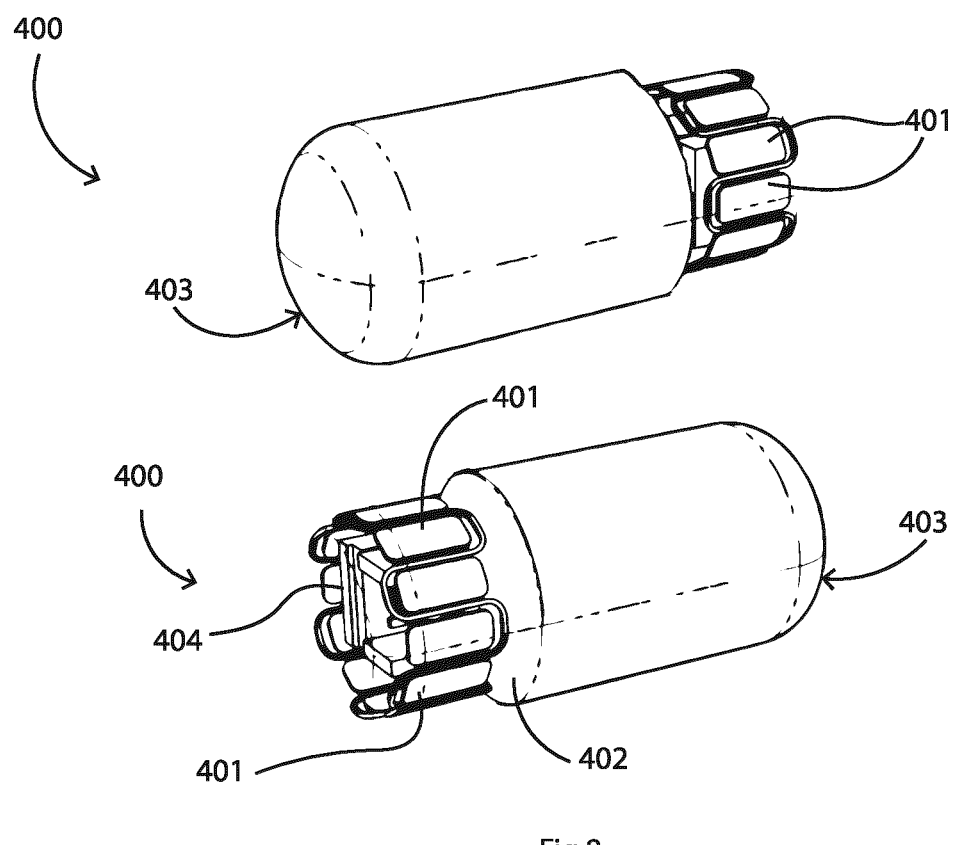
FIG. 8 is a pair of perspective views of a capsule with pressure sensors.
Figure 9:
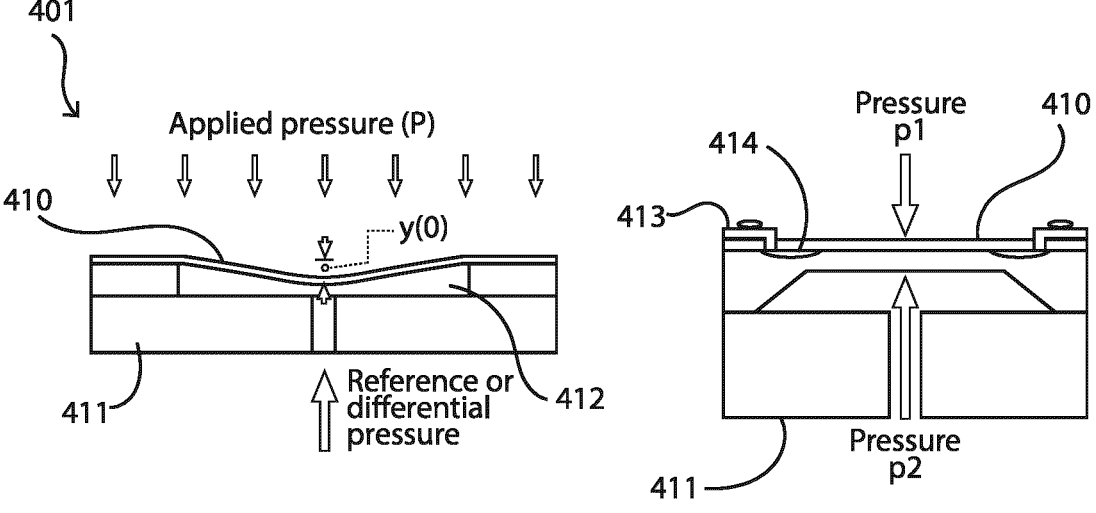
FIG. 9 shows operation of the pressure sensors.
Figure 10:
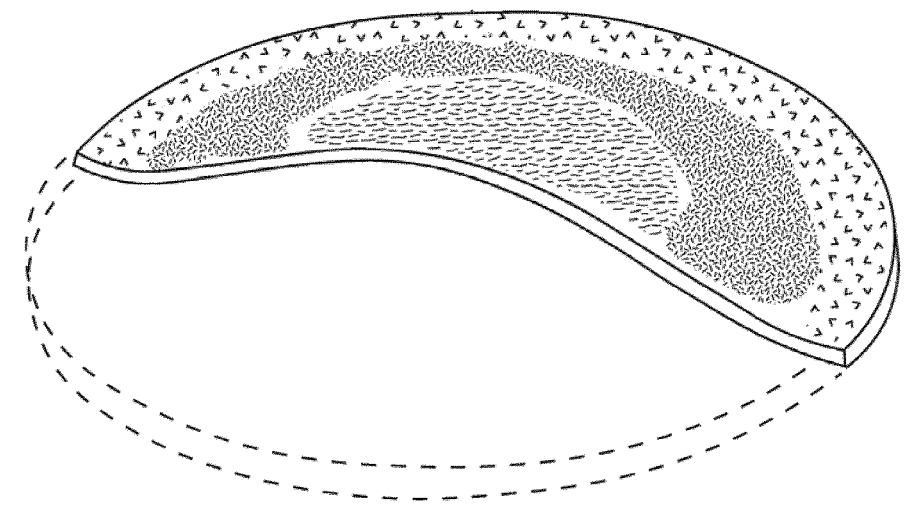
FIG. 10 illustrates deformation of a diaphragm of a pressure sensor when pressure is applied.

FIGS. 8 to 10 show embodiments of a capsule having pressure sensors. As shown in FIGS. 8 to 10, a capsule 400 comprises a circumferentially arranged series of pressure sensors 401 in a recessed tubular part 402/404 of a housing 403 at one end. The pressure or force as the capsule passes through the GI tract varies and the sensing element reacts to the local force or pressure, providing an output signal that can be interpreted by the microprocessor. Each pressure sensor 401 comprises a diaphragm 410 and a strain gauge 411 which provide an output as the deflection of the diaphragm 410 is caused. The diaphragm 410 is mounted on a strain gauge 411 which defines a cavity 412 behind the diaphragm 410, and there are contacts 413 on either side and linked to Wheatstone Bridge variable resistors 414 the resistance of which varies with deflection of the diaphragm 410. The output can vary from 1 mV/V) to 30 mV/V. The full-scale output is determined by multiplying the output of the sensor by the voltage used to power the sensor. For example, for a 3 mV/V sensor and a 10V DC excitation voltage there is an output of 3 mV/V×10V=30 mV at full scale. FIG. 10 shows by grey scales the reaction of the diaphragm when pressure is applied, the lighter the shade the greater the deflection.

The pressure from the GI Tract being measured is applied to the diaphragm 410, causing the deflection of the diaphragm as shown in FIG. 10, stressing the Wheatstone bridge arrangement 414, and creating a mV/V output. This millivolt signal is then read by the capsule's processor and/or is transmitted to the external receiver. The strain gauges are configured in a Wheatstone bridge where all four resistors are equal, and change by equal magnitude proportionally, when strain is applied. The greater the force or strain (input), the greater the output. The Wheatstone bridge has four wires for its connection, positive and negative excitation, and positive and negative sensor output.

Figure 11:
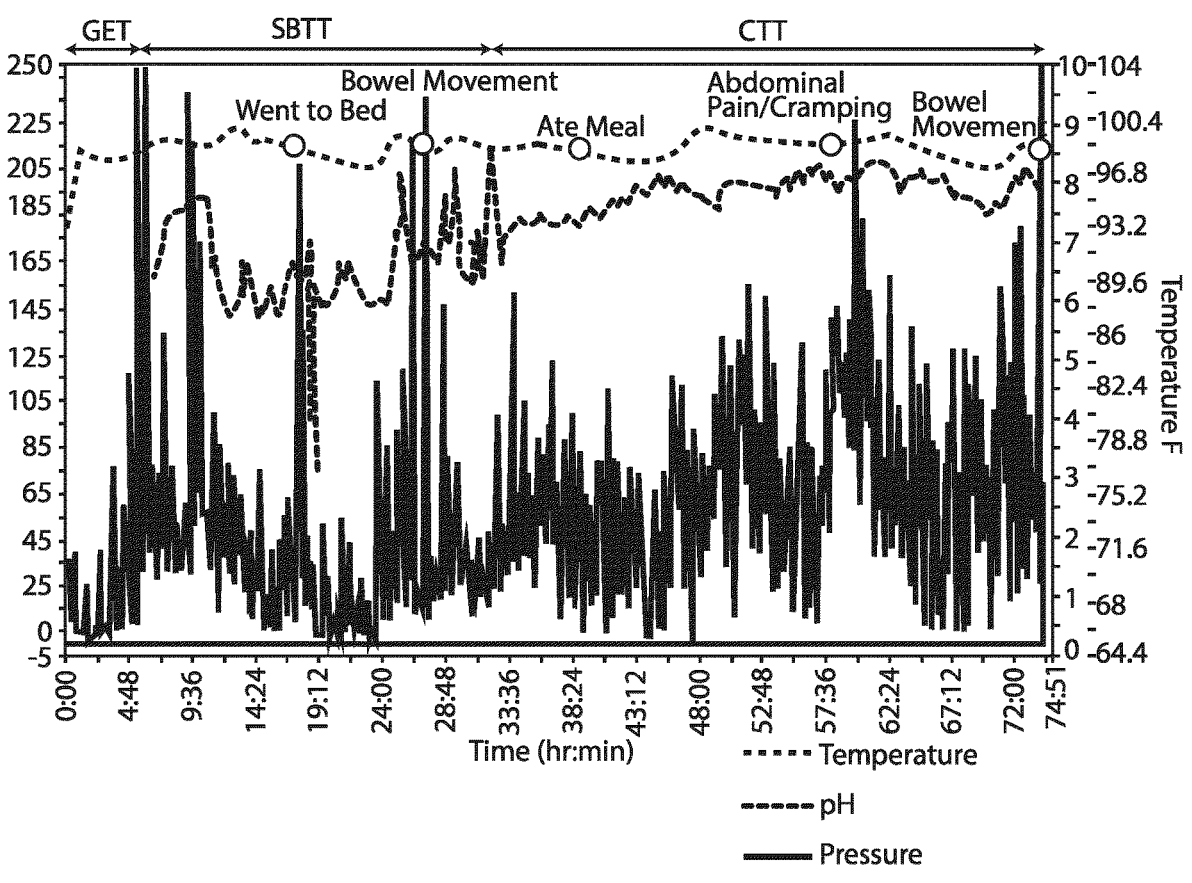
FIG. 11 is a plot showing pressure differences according to location in the GI tract.

FIG. 11 shows a pressure profile of the GI tract, this information enabling position of the capsule in the GI tract to be determined. In the case of an anchored capsule, the monitoring of pressure can be used to determine when it has dislodged and therefore is now moving through the GI tract. The host processor monitors the pressure profile from ingestion or from an anchored position.

A combination of pH sensors and pressure sensors provide an even more accurate determination of positioning of the capsule because the pressure sensor will spike as it goes through sphincteric valves as illustrated in FIG. 11.

The onboard processor and/or the external host receiver processor may combine the pressure-derived position estimation with data derived from other sensors. For example, the processor may generate a map associating blood data with GI location data.

For example, if the capsule measures an abrupt rise in pH (>2 pH units), associated to a rise to the pressure from 5-80 mmHg to 125-250 mmHg, this indicates a capsule passage from the stomach. If the optical sensor detects blood after these conditions have been met, this indicates that the source of blood is after the stomach.

A pressure sensor placed on the housing of the capsule, as described above, may be advantageous in that it may inform how much liquid is surrounding the capsule (pressure=ρg H at the bottom of the stomach).

The orientation of the capsule may be detected, to determine, for example, an unwanted situation such as not enough liquid around the capsule, the capsule being lodged in the GI tract, or a sensing channel being obstructed. Also, if the capsule is going through a valve, then there is higher risk of misdiagnosis.

Optical Sensor in Combination with a Camera

Figures 12, 13:
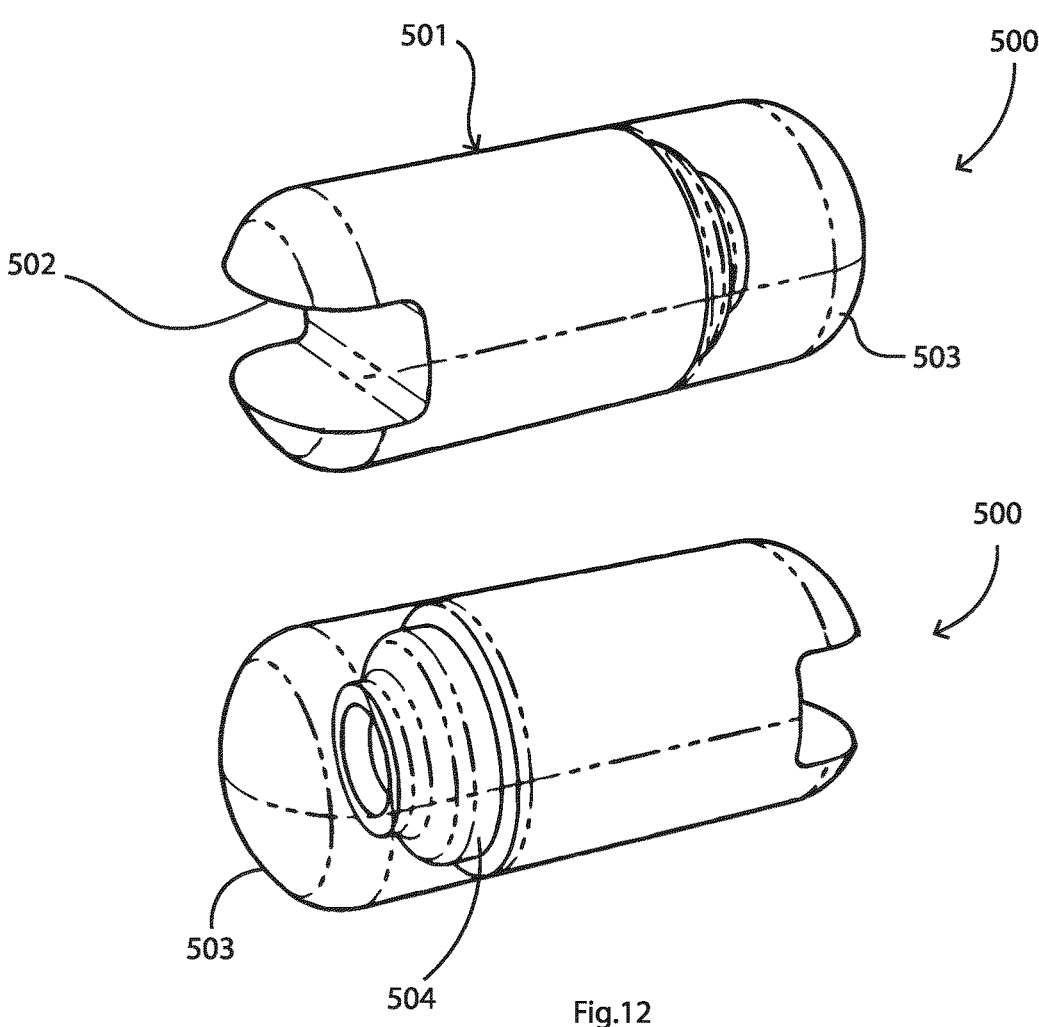
FIG. 12 is a pair of perspective views showing a capsule with a camera facing one end.
FIG. 13 shows sequencing of operation of the camera and the LED radiation sensors to avoid interference.

Referring to FIG. 12, a capsule 500 has a housing 501 with a radiating-sensing sensing volume 502 at one end, and this may be configured with radiation sensors as described in any example above (e.g., an emitter and detector arranged facing a sensing volume defined by walls, e.g., planar, convex, or concave transparent walls, e.g., of a recess in the housing). At the opposite end there may be an optically transparent domed end 503 of the housing within which there is a camera 504. The domed end 503 may be of a plastic material (e.g., a plastic suitable for the transparent walls, as described herein), for example, which is transparent to visible-wavelength radiation, as for any of the transparent walls described above.

The radiation sensor at the sensing volume 502 is situated so that it is exposed to the same area of the GI tract as the camera 504. The onboard processor controls the camera to continuously take images, however it is multiplexed with the radiation sensor to avoid cross-talk, as shown in FIG. 13. The clocks are synchronised between the camera and the optical sensor.

As shown in FIG. 12 the camera is directed in longitudinally. However, in other examples it may be directed laterally, towards the lumen.

Figure 14:
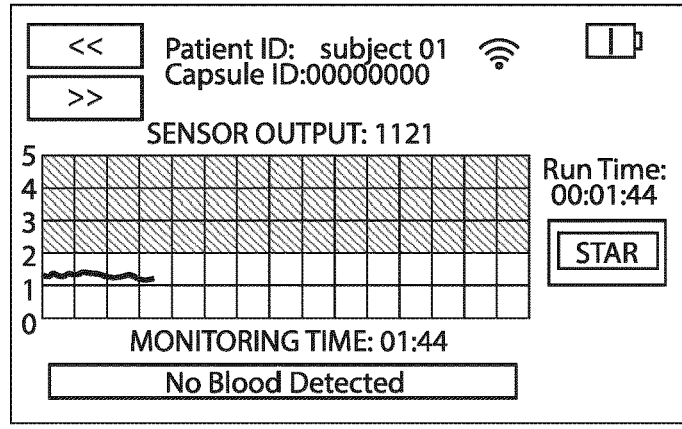
FIG. 14 shows two plots of outputs derived from camera image data together with sample images.
Figure 14:
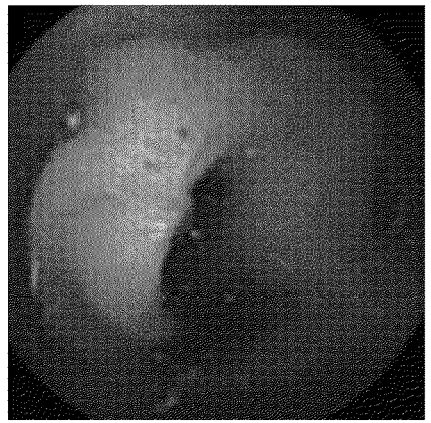
Figure 14:
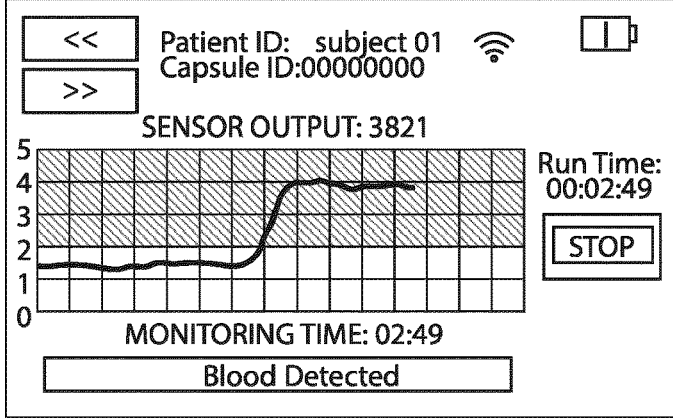
Figure 14:
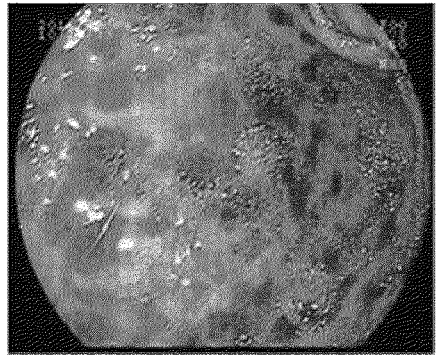

The camera can be activated when a sensor registers a value, for example using pH to determine where in the GI tract the camera is located and only activating the camera in that area. For example, the system uses a combination of an optical sensor and another sensor such as a pH sensor, or a pressure sensor, or a temperature sensor to activate the camera and to determine whether to activate video or still photographs. In another example, an optical sensor for blood detection may trigger a date and time stamp on the visual data for a camera in the capsule. FIG. 14 shows sample outputs from the optical sensor and the camera. In the top image the optical sensor shows an output below the threshold confirming the absence of blood displayed from the camera. In the bottom image the optical sensor shows an output above the threshold confirming that the red colour displayed by the camera is blood.

In an alternative arrangement, when red colour is visualised by the camera, the microcontroller activates the optical sensor to analyse the light spectrum to check if that is blood/gastric fluid/gastric fluid with other pancreatic enzymes and/or bile.

An image capture by the camera may be used to confirm a result detected by another sensor.

Sensing Units Mounted to a Catheter

In some examples of the invention the sensor system comprises a biosensor and an external host with a processor linked wirelessly. However, the link may be wired.

Figure 15:
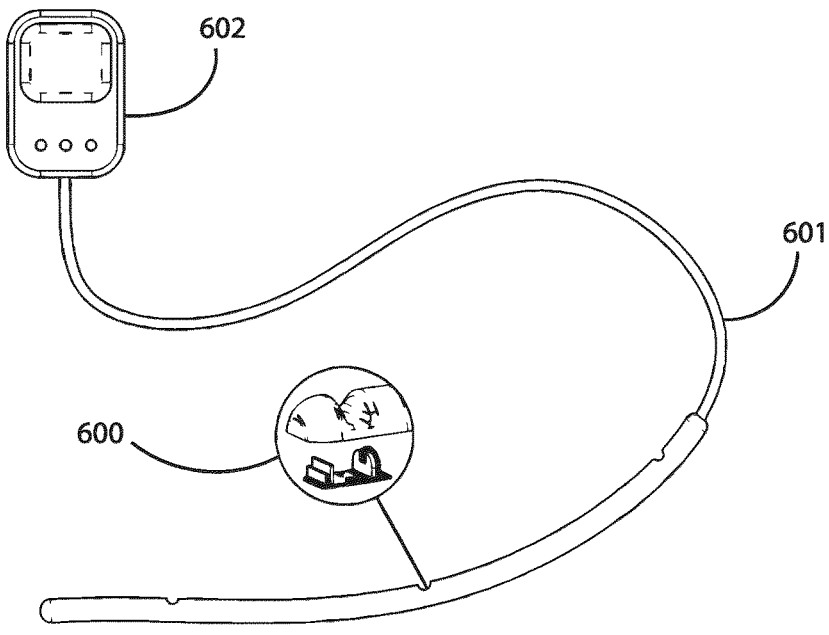
FIG. 15 is a view of a sensing system including a catheter supporting a number of modified sensing units along its length, each of which is a modified capsule.

As shown in FIG. 15 sensing units 600 may be mounted along the length of a catheter 601 linked at its proximal end with a controller 602. Each sensing unit 600 includes a housing with a sensing volume and/or any combination of radiation, pressure, pH, temperature, and image sensor described above. Each sensing unit 600 need not have an antenna or a battery and associated electronic components. Power and control and data signals may be provided by a lead in a lumen of the catheter. The sensing functionality can be as described for a capsule of any embodiment, the difference being that the capsule does not move along the GI tract on its own, rather it provides a desired set of readings for its known location once the catheter is in place, and the data can be provided by wire along the catheter, avoiding need for an antenna and/or batteries in some embodiments. The sensors can be mounted in a catheter of small diameters (<8 mm) to be inserted thought intubation kit, working channel of an endoscope or simply inserted into external drain tube to identify the presence of blood post-surgical operation.

Temperature Sensor

The capsule may include a temperature sensor to provide useful additional data, and they may be used to detect that the capsule is no longer in the body, by a sudden drop in sensed temperature.

Capsule Orientation Control

In some of the examples described there is asymmetric weight distribution of the capsule along the longitudinal axis. The asymmetric weight distribution may in some cases be achieved by locating the batteries 5 at one end, providing more weight at that end. Such a weight distribution helps to orientate the capsule with the heavier end facing downwardly in use. Alternatively, a ballast element, e.g., a metal ball or ring, may be located at one end. Ballasts may also be used to ensure full submersion of the capsule (e.g., in the stomach).

There may be additional orientation-control elements, as described below.

Figures 18, 19:
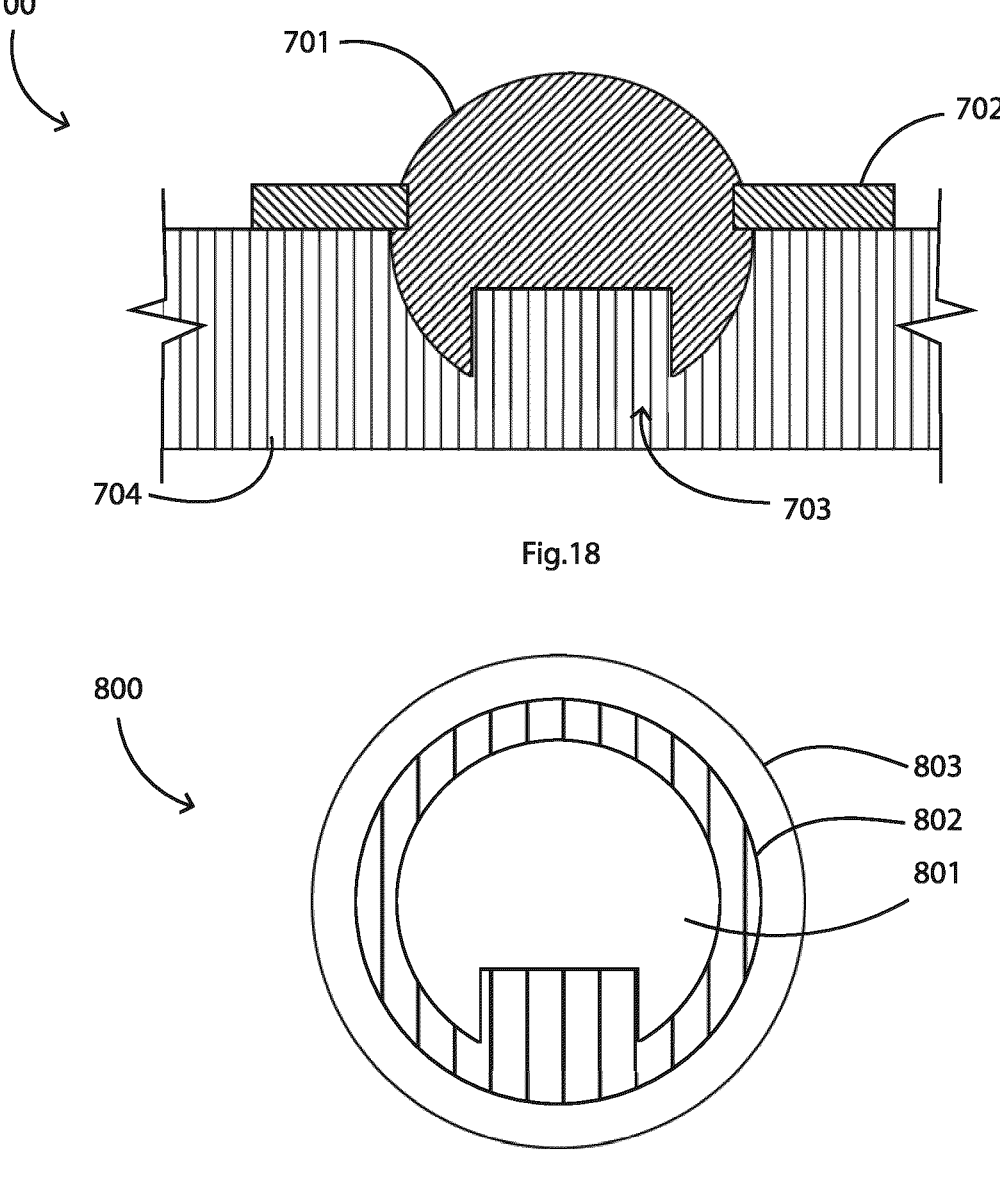
FIG. 18 is a diagram showing a capsule with a buoyancy element to assist correct orientation for immersion of the housing with sensors.
FIG. 19 is a diagrammatic cross-sectional view of a capsule with an adhesive layer for retention at a location.

Referring to FIG. 18, in some examples the capsule may have a buoyant structure around the housing to ensure that it always has a desired orientation. The structure is buoyant, so that, in some instances, about half of the capsule is floating while that part with the sensors is immersed at all times. A capsule 700 has a housing 701 and a belt 702 extending along and around the long circumference, thus ensuring that a region 703 is immersed. The belt 702 may be of any suitably buoyant material (e.g., of lower density that water, e.g., Styrofoam and/or polystyrene). A capsule may contain a combination of ballast and buoyant elements.

Retention Mechanism

Capsules of the invention may include a retention mechanism, or elements of a retention mechanism, for example, an eyelet for sutures, an adhesive element, or a magnetic element.

A biodegradable suture put in place endoscopically or laparoscopically may be trained through an eyelet of the housing. The biodegradable suture is designed to retain the capsule for 2 to 20 days, preferably 3-7 days. The advantage is that this enables monitoring in a single position and orientation for a prolonged period of time. Following degradation of the suture, the capsule may continue through the GI tract, with or without monitoring. The suture may be non-biodegradable, or biodurable, in some embodiments.

There may be a magnet providing an attraction force in a range of 2N to 25N (by for example an external patch and/or belt) and placed in such a way that the capsule is retained in the stomach. A pressure sensor may detect if the capsule is in contact with tissue (but not perforating it) and the pH sensor will help identify location.

As shown in FIG. 19, a capsule 800 has a housing 801, an adhesive layer 802, and an outer sacrificial layer 803 which biodegrades under the pH conditions of the GI tract to expose the adhesive layer 802. These materials could be for example PLLA or PCL. Following degradation of the sacrificial layer 803, the adhesive layer 802 may be free to temporarily adhere to the lining of the selected portion of the GI tract.

In general, prolonged monitoring at a particular site may be achieved by use of a retention mechanism using one or more of a suture element, a magnet-based system, or an adhesive layered system.

Processor Operation to Combine Detection Data Streams

The above description sets out manners of combining different detection data streams from different sensors. These aspects may be summarised as follows.

Detection data from two or more of radiation (for example optical), pH, temperature, image (camera), and pressure sensors can be combined by the processor (either onboard or external or both) to provide outputs such as:

Capsule location, especially with the benefit of pH, pressure and temperature detection data.

Fresh versus old blood by using optical sensor alone or in conjunction with pH sensor Concentration of blood by using optical sensor alone or in conjunction with pH sensor Information on transit and location, for example using pressure detection data.

Feedback to determine whether the capsule is in liquid by using a pressure sensor.

Pressure profile to determine the validity of data collected by the optical sensor, for example when the optical sensor is passing through the pylorus there may be spikes of blood detected, however these may be false positive results.

To inform if the capsule is lodged in the GI tract, for example using temperature data, and temperature changes may indicate if the capsule has left the body.

A command for activation of the camera based on the feedback of one of the other sensors.

Activation of the camera may allow gathering of a video stream for a particular part of the GI tract, for example activating it in the lower intestine based on pH data and/or pressure profile data.

a command for Activating the camera for spectro-analysis to verify the presence of blood or bile.

A command for activating the camera to take video or still images of a region, for example in a prolonged monitoring the sensor can activate the camera and time stamp the event.

ALTERNATIVE EMBODIMENTS

The invention is not limited to the embodiments described but may be varied in construction and detail. Components of the capsules of various embodiments may be combined in different manners to suit the circumstances. For example, different combinations of radiation wavelengths may be used. The radiation wavelengths may be different from those described, potentially further outside the visible spectrum. Also, it is not essential that the antenna is all or partly within the housing. It is envisaged that it may be at least partly externally mounted, and some of it may be embedded within the housing material. The radiation emitter drive circuit and the signal processing circuit linked to the detector may have any desired level of data processing capabilities, ranging from the basic for driving the emitter and receiving signals from the detector to more comprehensive processing. Where the level is basic more processing would be performed on the external receiver with which the capsule communicates. On the other hand, the system may comprise only the capsule, with the signal processing circuit being configured to transmit full-processed signals for reception by an external computing device.

For example, instead of having radiation emitters and receivers on opposed sides of a sensing volume, they may be located elsewhere in the housing, and optic fibres may be arranged to direct light to the relevant transparent part of the housing. The alternative arrangement would have the benefit of the active electronic components all being mounted on fewer, such as a single, substrate. In another example, the sensors and the processor are arranged to identify another capsule in order to prevent misdiagnosis. This is achieved by the photo detector detecting an intensity of radiation within the GI tract, which can only arise because there is another capsule present.

Components of embodiments can be employed in other embodiments in a manner as would be understood by a person of ordinary skill in the art. The invention is not limited to the embodiments described but may be varied in construction and detail.

The invention claimed is:

1. A biosensor system comprising:
(a) biosensor comprising:
a housing configured for insertion in a mammalian gastrointestinal GI tract;
a plurality of sensors including:
a first sensor comprising at least one radiation emitter arranged to emit radiation to the environment outside the housing and a radiation detector arranged to detect radiation from the environment, wherein the housing has at least one portion which is transparent to sensing radiation, and the first sensor is arranged to emit radiation through the housing to the environment outside the housing and to detect radiation from the environment through the transparent portion of the housing,
at least one additional sensor for detection of a condition in the environment, wherein the at least one additional sensor comprises at least one pressure sensor providing pressure detection data,
a drive circuit for controlling the sensors, and
a data transmitter for transmission of detection data received by the plurality of sensors, and
(b) a processor linked with the sensors for processing the detection data in combination to provide information about said biosensor environment, wherein the processor is configured to use said pressure detection data in combination with first sensor detection data to determine if the biosensor is lodged in the GI tract with a sensing channel obstructed and/or if the biosensor is going through a valve, and
wherein the processor is configured to determine from said first sensor an indication of presence of a particular fluid according to determining an angle as an arctan of a wavelength difference divided by a difference in detected signal and comparing said determined angle with a threshold angle.

2. The biosensor system as claimed in claim 1, wherein the drive circuit is configured to activate the sensors with time separation to prevent interference; and wherein the first sensor is arranged to emit radiation into a sensing volume formed by a recess of the housing, the sensing volume being open to access by fluids in said environment.

3. The biosensor system as claimed in claim 1, wherein at least one additional sensor comprises an electrical pH sensor providing pH detection data.

4. The biosensor system as claimed in claim 1, wherein the at least one pressure sensor comprises a diaphragm having an external surface, wherein deflection of said diaphragm indicating local pressure.

5. The biosensor system as claimed in claim 1, wherein there are a plurality of pressure sensors each mounted in a longitudinal direction to face radially and are arranged circumferentially around the housing.

6. The biosensor system as claimed in claim 1, wherein there are a plurality of pressure sensors each mounted in a longitudinal direction to face radially and are arranged circumferentially around the housing; and wherein the pressure sensors are mounted in a narrowed portion of the housing.

7. The biosensor system as claimed in claim 1, further comprising a buoyant element mounted to an external surface of the housing to bias it to an orientation with sensors immersed in liquid.

8. The biosensor system as claimed in claim 1, further comprising a buoyant element mounted to an external surface of the housing to bias it to an orientation with sensors immersed in liquid; and wherein the buoyant element surrounds the housing in the longitudinal direction.

9. The biosensor system as claimed in claim 1, wherein the transmitter includes an antenna which is mounted in a domed end of the housing, and is the form of a spiral with decreasing diameter in a direction towards an end of the housing, and wherein the antenna has a maximum radial dimension in the range of 7.5 mm to 9 mm and it narrows to form an apex with a radial dimension in the range of 2 mm to 4 mm, and wherein the transmitter comprises RF circuits located adjacent to the antenna, on a substrate extending longitudinally.

10. The biosensor system as claimed in claim 1, wherein the first sensor comprises a plurality of optical emitter devices each adapted to emit at a particular wavelength and the drive circuit is configured to activate each emitter device according to a time multiplex scheme, and the time separation between activations is in the range of 2 ms to 5 ms, and wherein the biosensor includes a light-absorbing guide surrounding a path between the radiation emitter and the detector of said first sensor and the housing.

11. The biosensor system as claimed in claim 1, wherein the processor is configured to determine an indication of presence of a particular fluid according to a ratio of detected signal of said first sensor for one emitter wavelength to that of another emitter wavelength, and wherein there is a particular ratio threshold for each of a plurality of combinations of radiation wavelengths.

12. The biosensor system as claimed in claim 1, wherein the processor is configured to determine an indication of presence of a particular fluid according to a ratio of detected signal of said first sensor for one emitter wavelength to that of another emitter wavelength, and wherein there is a particular ratio threshold for each of a plurality of combinations of radiation wavelengths; and wherein the said combinations include one or more of: red:green, far red: green, red:blue, far red:blue, far red:red.

13. The biosensor system as claimed in claim 1, wherein the processor is configured to determine from said first sensor detection data a severity value for an indication of presence of a particular fluid according to detected signal amplitude for one or more radiation wavelengths, and wherein the said severity value is an indicator of extent of internal bleeding.

14. The biosensor system as claimed in claim 1, wherein the processor is configured to use detection data from at least one of said additional sensor or sensors to select an algorithm to calculate blood concentration.

15. The biosensor system as claimed in claim 1, wherein the additional sensor comprises a pH sensor, and the processor is configured to process detection data from the first sensor and from the pH sensor to generate data concerning what radiation sensor wavelength to activate.

16. The biosensor system of claim 1, wherein the additional sensor comprises two or more of: pH, temperature, image, and pressure sensors, and the processor is configured to use detection data from said first sensor and said additional sensors to provide any one or more of the following outputs:

biosensor location;

determination as to whether detected blood is fresh or old blood;

concentration of fluid around the capsule;

information on biosensor transit and location;

whether the biosensor is in liquid;

determination of validity of data collected by the radiation sensor;

determination if the capsule is lodged in the GI tract;

a command for activation of the camera based on detection data from a sensor other than the camera;

a command for activating the camera for spectro-analysis to verify the presence of blood or bile; and/or a command for activating the camera to take video or still images of a region.

24

17. A biosensor system comprising:

(a) biosensor comprising:

a housing configured for insertion in a mammalian gastrointestinal GI tract;

a plurality of sensors including:

a first sensor comprising at least one radiation emitter arranged to emit radiation to the environment outside the housing and a radiation detector arranged to detect radiation from the environment, wherein the housing has at least one portion which is transparent to sensing radiation, and the first sensor is arranged to emit radiation through the housing to the environment outside the housing and to detect radiation from the environment through the transparent portion of the housing, at least one additional sensor for detection of a condition in the environment, wherein the at least one additional sensor comprises at least one pressure sensor providing pressure detection data, a drive circuit for controlling the sensors, and a data transmitter for transmission of detection data received by the plurality of sensors, and (b) a processor linked with the sensors for processing the detection data in combination to provide information about said biosensor environment, wherein the processor is configured to use said pressure detection data in combination with first sensor detection data to determine if the biosensor is lodged in the GI tract with a sensing channel obstructed and/or if the biosensor is going through a valve, and wherein the processor is configured to, using detection data from said first sensor, determine a proportion of fall in detected signal strength for one or more emitter wavelengths as a parameter in determining the severity value; and wherein the processor is configured to use different light wavelengths to distinguish new blood from old blood; and wherein the processor is configured to use a ratio of two wavelengths to indicate old blood and a ratio of different wavelengths to indicate fresh blood.

18. A biosensor system comprising:

(a) biosensor comprising:

a housing configured for insertion in a mammalian gastrointestinal GI tract;

a plurality of sensors including:

a first sensor comprising at least one radiation emitter arranged to emit radiation to the environment outside the housing and a radiation detector arranged to detect radiation from the environment, wherein the housing has at least one portion which is transparent to sensing radiation, and the first sensor is arranged to emit radiation through the housing to the environment outside the housing and to detect radiation from the environment through the transparent portion of the housing, at least one additional sensor for detection of a condition in the environment, wherein the at least one additional sensor comprises at least one pressure sensor providing pressure detection data, a drive circuit for controlling the sensors, and a data transmitter for transmission of detection data received by the plurality of sensors, and (b) a processor linked with the sensors for processing the detection data in combination to provide information about said biosensor environment, wherein the processor is configured to use said pressure detection data in combination with first sensor detection data to determine if the biosensor is lodged in the GI tract with a sensing channel obstructed and/or if the biosensor is going through a valve, and wherein the processor is configured to use pressure sensor detection data to estimate the extent of liquid surrounding the biosensor.

19. A biosensor system comprising:

(a) biosensor comprising:

a housing configured for insertion in a mammalian gastrointestinal GI tract;

a plurality of sensors including:

a first sensor comprising at least one radiation emitter arranged to emit radiation to the environment outside the housing and a radiation detector arranged to detect radiation from the environment, wherein the housing has at least one portion which is transparent to sensing radiation, and the first sensor is arranged to emit radiation through the housing to the environment outside the housing and to detect radiation from the environment through the transparent portion of the housing, at least one additional sensor for detection of a condition in the environment, wherein the at least one additional sensor comprises at least one pressure sensor providing pressure detection data, a drive circuit for controlling the sensors, and a data transmitter for transmission of detection data received by the plurality of sensors, and a processor linked with the sensors for processing the detection data in combination to provide information about said biosensor environment, wherein the processor is configured to use said pressure detection data in combination with first sensor detection data to determine if the biosensor is lodged in the GI tract with a sensing channel obstructed and/or if the biosensor is going through a valve, and wherein the processor is configured to use a pH-specific algorithm to calculate blood concentration; and wherein the processor is configured to select a blood concentration on the basis that a ratio of Red transmitted light to orange transmitted light in the range of 1 to 1.5 indicates a low concentration of blood, while a value in a range of 2 to 10 indicates a medium concentration of blood, and a value greater than 10 indicate a high concentration of blood.

* * * * *